US008856150B2

(12) United States Patent
Machtelinck

(10) Patent No.: US 8,856,150 B2
(45) Date of Patent: Oct. 7, 2014

(54) MANAGING AND DISPLAYING SOLUTIONS FOR MULTIPLE RESOURCES IN AN APPOINTMENT SCHEDULING SYSTEM

(75) Inventor: Geert Machtelinck, Mortsel (BE)

(73) Assignee: Agfa HealthCare Inc., Ontario (CA)

( * ) Notice: Subject to any disclaimer, the term of this patent is extended or adjusted under 35 U.S.C. 154(b) by 1389 days.

(21) Appl. No.: 11/817,650

(22) PCT Filed: Feb. 17, 2006

(86) PCT No.: PCT/EP2006/060036
§ 371 (c)(1),
(2), (4) Date: Sep. 20, 2007

(87) PCT Pub. No.: WO2006/094882
PCT Pub. Date: Sep. 14, 2006

(65) Prior Publication Data
US 2008/0222541 A1    Sep. 11, 2008

Related U.S. Application Data

(60) Provisional application No. 60/666,264, filed on Mar. 29, 2005.

(30) Foreign Application Priority Data

Mar. 4, 2005 (EP) .................................... 05101679
Mar. 4, 2005 (EP) .................................... 05101703

(51) Int. Cl.
*G06F 7/00* (2006.01)
*G06F 17/30* (2006.01)
*G06Q 50/22* (2012.01)
*G06F 19/00* (2011.01)
*G06Q 10/10* (2012.01)

(52) U.S. Cl.
CPC .............. *G06Q 50/22* (2013.01); *G06F 19/327* (2013.01); *G06Q 10/109* (2013.01); *Y10S 707/951* (2013.01)
USPC .......................................... 707/754; 707/951

(58) Field of Classification Search
CPC .................................................. G06F 17/30867
USPC .................................................. 707/754, 951
See application file for complete search history.

(56) References Cited

U.S. PATENT DOCUMENTS 5,860,067 A      1/1999  Onda et al.
6,466,236 B1 *  10/2002  Pivowar et al. ................ 715/835
(Continued)

FOREIGN PATENT DOCUMENTS

EP      0 306 965 A2     3/1989
EP      1 531 411 A1     5/2005
WO      02/101622 A1    12/2002

OTHER PUBLICATIONS

Anonymous, "Zooming in on Visual Calendar Data," Research Disclosure, Kenneth Mason Publications, Westbourne, GB, vol. 329, No. 19, Sep. 1991, one page.

(Continued)

*Primary Examiner* — Alexey Shmatov
(74) *Attorney, Agent, or Firm* — Keating & Bennett, LLP

(57) ABSTRACT

A solution space is computed and stored which comprises for a given set of constraints all possible solutions for all available resources of a certain kind. Upon selection of a specific resource, the solution space is filtered to select all possible combinations containing the specific resource and the result of the filtering is displayed.

11 Claims, 12 Drawing Sheets

(56) References Cited

U.S. PATENT DOCUMENTS

| | | | |
|---|---|---|---|
| 7,246,075 B1 * | 7/2007 | Testa | 705/8 |
| 7,502,747 B1 * | 3/2009 | Pardo et al. | 705/8 |
| 2003/0016248 A1 | 1/2003 | Ubillos | |
| 2004/0024616 A1 * | 2/2004 | Spector et al. | 705/2 |
| 2005/0004815 A1 | 1/2005 | Machtelinck | |
| 2005/0234741 A1 * | 10/2005 | Rana et al. | 705/2 |
| 2007/0112610 A1 * | 5/2007 | Johnson et al. | 705/8 |

OTHER PUBLICATIONS

Bassat, Ben M., et al., "The W-6 approach to multi-dimensional scheduling: where AI and operations research meet," Proceedings of the International Conference on Systems, Man, and Cybernetics, Los Angeles, Nov. 4-7, 1990, New York, IEEE, US, Nov. 4, 1990, pp. 276-281.

ILOG White Papers, "ILOG Optimization Suite," May 2001, pp. 1-61.

Institute of Medicine, "Crossing the Quality Chasm: A New Health System for the 21st Century," National Academy Press, Washington, D.C., 2001, cited pp. 3, 4, 6, 12 and 127.

Oddi, A., et al., "Toward interactive scheduling systems for managing medical resources," Artificial Intelligence in Medicine, vol. 20, No. 2, Oct. 2000, pp. 113-138.

Pollack, Martha E., et al., "Execution-Time Plan Management for a Cognitive Orthotic System," Lecture Notes in Computer Science, vol. 2466, Jan. 2002, pp. 179-192.

Schwalb, E., et al., "Temporal Constraints: A Survey," Constraints: An International Journal, vol. 3, No. 2, Jun. 1998, pp. 129-149.

European Search Report from EP 05101682, Report dated Nov. 14, 2005, 10 pages.

International Search Report from PCT/EP2006/060036, filed Feb. 17, 2006, Report amiled Jun. 4, 2006, 8pgs.

International Search Report from PCT/EP2006/060038, filed Feb. 17, 2006, Report mailed Sep. 28, 2007, 3pgs.

International Search Report from PCT/EP2006/060039, filed Feb. 17, 2006, Report mailed Jun. 16, 2006, 10pgs.

International Search Report from PCT/EP2006/060044, filed Feb. 17, 2006, Report mailed May 24, 2006, 8pgs.

International Preliminary Report on Patentability from PCT/EP2006/06044, filed Feb. 17, 2006, Report mailed Sep. 20, 2007, 7pgs.

European Search Report from EP 05101703 completed on Jun. 7 2005.

\* cited by examiner

RL: relational link; both actions are concurrent
CL: comprising link; parent action comprises children action
SL: sequential link; one action follows the other

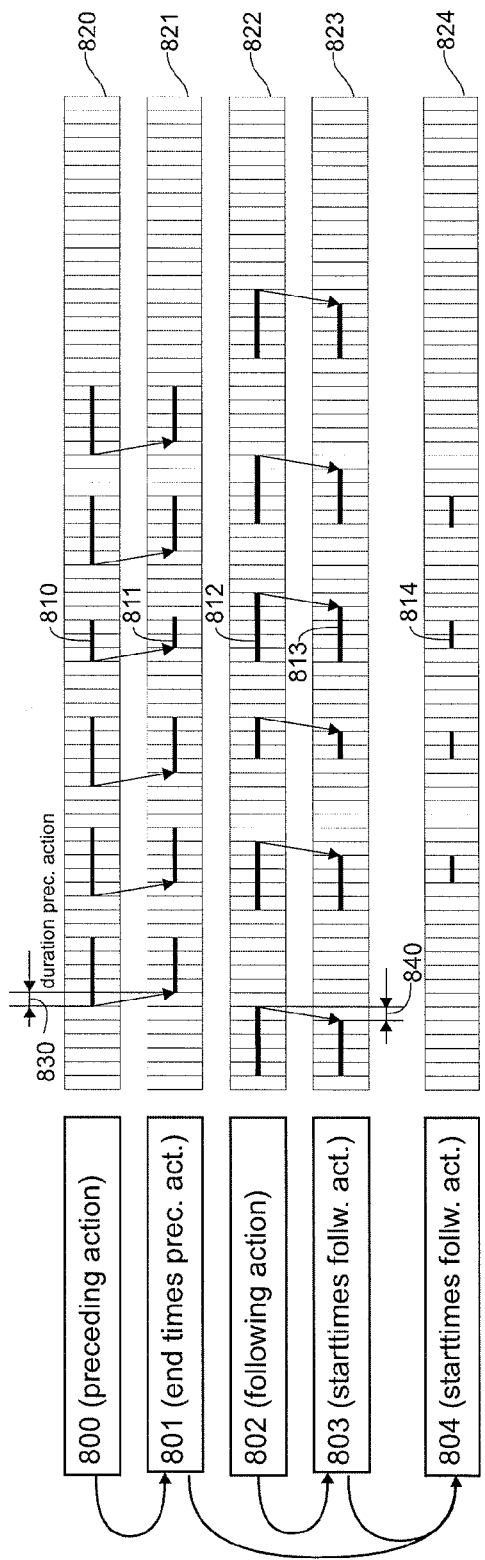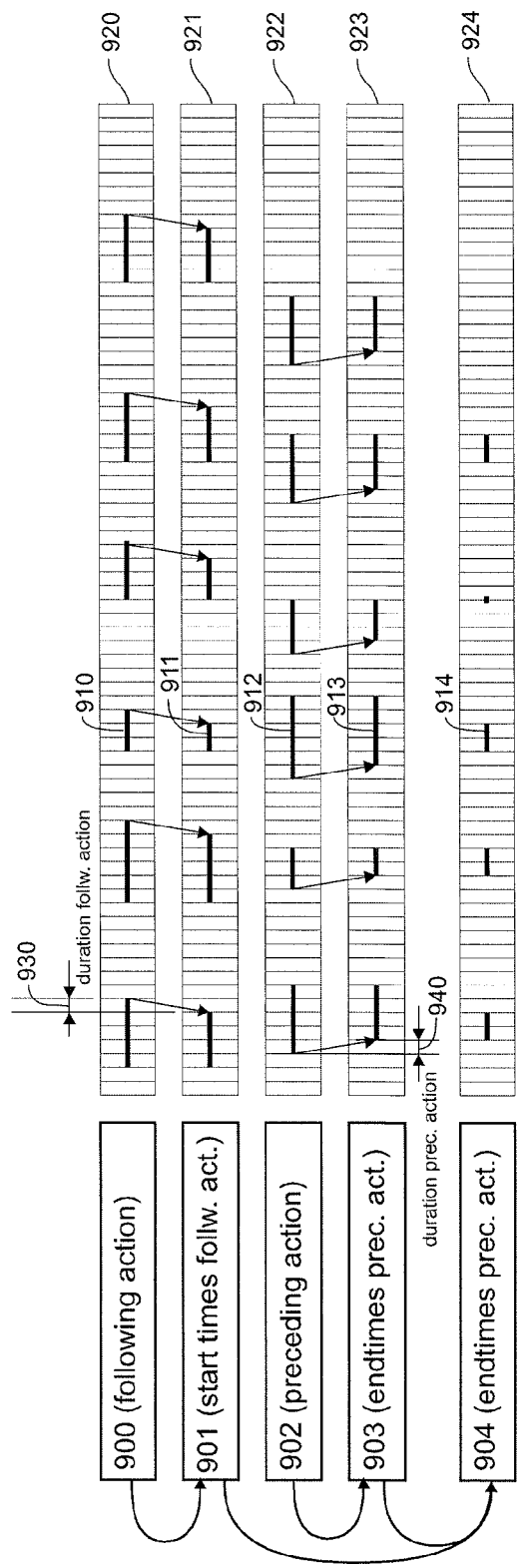

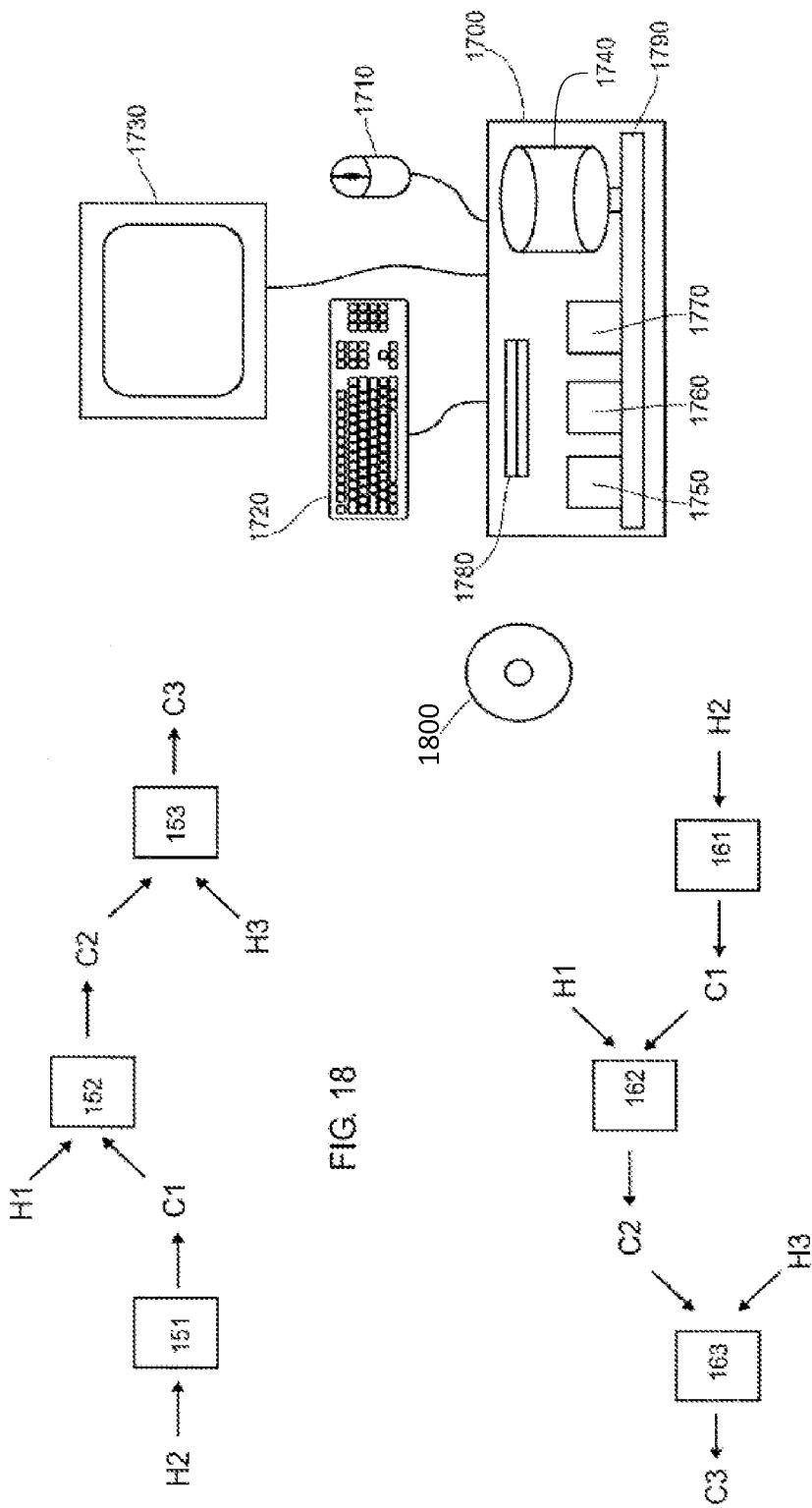

MANAGING AND DISPLAYING SOLUTIONS FOR MULTIPLE RESOURCES IN AN APPOINTMENT SCHEDULING SYSTEM

FIELD OF THE INVENTION

The present invention relates to an appointment scheduling system and a user interface for such a scheduling system.

The present invention more specifically relates to an appointment scheduling system for application in a situation in which multiple resources are available.

Appointment scheduling systems can be applied in medical institutions, where appointments need to be scheduled for patients, taking into account a multitude of constraints such as the availability of personnel and equipment, and of the patient himself.

BACKGROUND OF THE INVENTION

Multi-resource appointment scheduling implies that for multiple appointment solutions, different resources are at stake.

The user could limit the number of resources before searching for adequate solutions, but for a number of reasons he prefers not to do so.

Examples are:
Searching for the first available consultation for a cardiologist, gives a larger degree of freedom, than to limit the search to one specific cardiologist
In multi-site (multi-hospital) situations, one would like to know the first possible appointment for a similar procedure type, independent of the location. In other words, one cannot first look into one location, and then start alternative searches to find out if earlier solutions are available at other locations or not.

Additionally, when being confronted with the possible solutions, one would like to find a certain solution with the least possible cost (=time to find the desired solution). Typical situations the user would like to handle:
show me the first possibilities in time, independent from the resource
show me the first possibility for a specific resource (eg. the preferred cardiologist), but in case not satisfactory (eg. too far in the future), possibility to switch to the first possibility for another resource, or independent from resources
Finally, patient may have the following requests:
show me the first possible solution after 5 pm or before 8 am
I prefer Dr. A, but if not available on short term notice, Dr. B or else, give me an alternative
I prefer Hospital A (because it's the nearest by), then hospital B or else, give me the earliest possible solution Existing scheduling applications need to restart a search engine to be able to answer to the problem situations stated above. This combined with the unpredictability of each search and combined with the patient demands, enlarges substantially the cost for booking an adequate appointment.

Additionally, solutions are currently mostly presented on a list basis. Such lists are not practical when one has to retrieve a solution in time.

It is an aspect of the present invention to overcome the above-mentioned drawbacks of the prior art appointment scheduling systems.

SUMMARY OF THE INVENTION

To achieve the above aspects the present invention provides, in an appointment scheduling system, a method of managing appointment solutions for multiple resources comprising the steps of computing a solution space comprising for a given set of constraints all possible appointment solutions for all available resources of a certain kind, storing said solution space, upon selection of a specific resource, filtering said solution space to select all possible appointment solutions for said specific resource, and displaying the result of said filtering.

In the context of the present invention a solution space is a collection of all solutions that are applicable for a given resource taking into account a given set of constraints.

A solution is said to be a 'possible' solution when it expresses a time or time slot on which the constraints are met and the resources are available (the time or time slot is free) so that scheduling of an event on such a time or time slot is allowable.

Examples of resources applicable in the context of a scheduling system for medical applications are for example physicians, examination room (e.g. radiology room), examination device (e.g. CT scanner) etc.

Different types of resources may be identified. A first type may include doctors having a certain specialisation such as cardiologists, paediatricians etc.

Another type of resource may comprise all radiology rooms available in one hospital or in a multi-site situation.

Still alternative types are possible.

Examples of constraints have been widely enumerated in the introductory part of the description and include all kinds of constraints which relate to time and time slots.

State of the art scheduling systems are designed to optimize the critical path in a project, including taking into account variations of the duration individual tasks. When used as a tool for the purpose of scheduling appointments, they will produce one single solution. If more than one solution is needed, the method needs to be run again with different constraints. This approach is time consuming and inefficient from the viewpoint of number of calculations that are required. Furthermore the prior art techniques are not designed to manage the complexity of scheduling tasks and subtasks that arises from the fact that a given task can only be performed depending on the availability of certain staff and equipment.

The method of the present invention provides a scheduling system that does not come up with just one appointment but is able to calculate, preferably in one step, a complete set of alternatives.

The system of the present invention enables a patient or a medical staff member to make a preferred choice from a set of possible appointments.

The system is based on the computation of a complete solution space comprising for a given set of constraints all possible solutions for all available resources of a specific type.

This solution space is stored.

When a specific resource is selected, for example when a specific doctor is selected, the complete solution space can be filtered on a resource which comes down to slicing the solution space. This operation is a relatively fast operation which enables real time interactive filtering of the appointment solution space.

An example of a scheduling engine for an appointment scheduling system is described extensively in US Pat. Publ. No. US 2009/0276278 entitled 'Method for processing a linked list of time segments', filed by the same applicant on the day of filing of the present application.

The embodiments of the methods of the present invention are generally implemented in the form of a computer program product adapted to carry out the method steps of the present invention when run on a computer. The computer program product is commonly stored in a computer readable carrier medium such as a CD-ROM.

Alternatively the computer program product takes the form of an electric signal and can be communicated to a user through electronic communication.

Another aspect of the present invention relates to a user interface as set out in the appending claims and in the detailed description below.

Specific features for preferred embodiments of the invention are set out in the dependent claims.

Further advantages and embodiments of the present invention will become apparent from the following description and drawings.

BRIEF DESCRIPTION OF THE DRAWINGS

FIG. 11 demonstrates the processing of a sequential link with a preceding action according to a preferred embodiment;

FIG. 12 demonstrates the processing of a sequential link with a following action according to a preferred embodiment;

FIG. 18 shows an example of using deductive logic;

FIG. 19 shows an example of using inductive logic;

FIG. 20 shows a data processing system according to a preferred embodiment of the current invention.

DETAILED DESCRIPTION OF THE INVENTION

Figure 1:
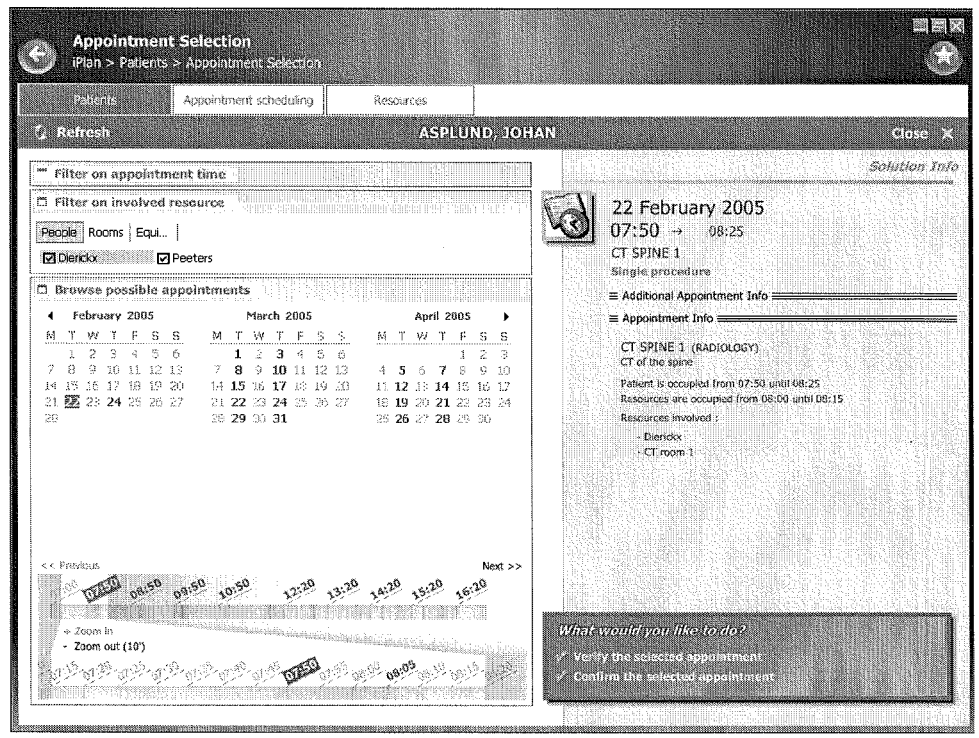
FIG. 1 shows a screen print displaying the user interface according to the present invention in a situation in which the results of the appointment scheduling procedure are shown when this procedure is applied for a single resource (in casu Dr. Dierickx)

FIG. 1 is a screen print of a user interface for an appointment scheduling system according to the present invention.

The user interface consists of a number of linked tabs each tab being dedicated to a specific operation. For example a first tab may be arranged for entering and displaying patient identification data, a second tab may be arranged for entering and displaying information relating to appointment scheduling and a third tab may be arranged for entering and displaying information on resources.

The different tabs may be selected and displayed sequentially on the screen of a display device.

Figure 2:
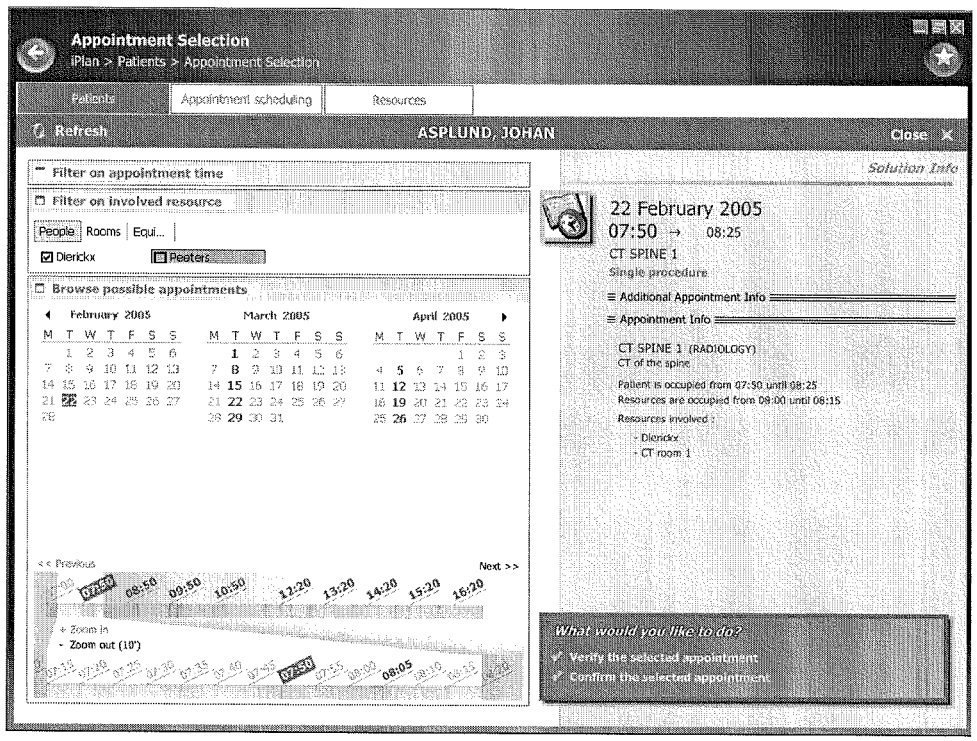
FIG. 2 shows a similar screen print as the screen print of FIG. 1 when applied for another resource (in casu Dr. Peeters)
Figure 3:
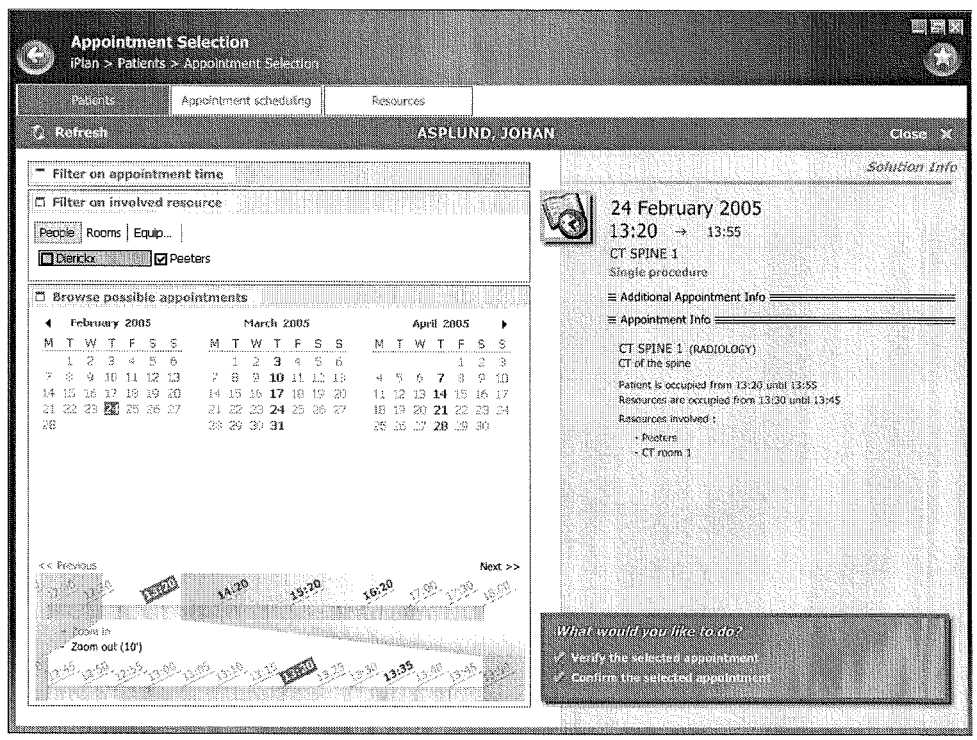
FIG. 3 shows a screen print displaying the user interface according to the present invention in a situation in which the results of the appointment scheduling procedure are shown when this procedure is applied for more than one resource.

The specific embodiment of the user interface according to the present invention which is shown in FIGS. 1-3 also has a horizontal bar in which the subpart of the scheduling application the operator is working with is displayed.

The user interface also has a second horizontal bar displaying the name of the patient to whom the current scheduling operation pertains.

In a first window—in this embodiment situated on the left side of the screen—selections can be made pertaining to people, rooms, equipment.

In a second window, in this application displayed simultaneously with the first window on the right side of the screen—an overview of details relating to the patient, the resources and/or the appointment is displayed.

According to the invention the user interface has selection means which upon activation provide input to the appointment scheduling system on the selection of a particular resource.

In the embodiment shown in FIGS. 1-3 this selection means is implemented in the form of a number of checkboxes adjacent to the display of the names of the resources which can be selected by checking one of the boxes.

In the figures the names of two doctors are shown adjacent to the checkboxes, one or either of the doctors can be selected by checking the corresponding checkbox(es).

The user interface further comprises a scheme pertaining to the availability of a resource which has been selected by checking the corresponding box. In the illustrated embodiment this scheme is implemented in the form of a displayed calendar.

In FIG. 1 doctor Dierickx has been selected and a calendar is shown on which the dates on which doctor is Dierickx is available are high-lighted.

FIG. 2 shows a similar scheme pertaining to doctor Peeters.

Upon activation of a selection means, more specifically as soon as one of the boxes is checked, the information on the selected resource is input to the scheduling system and a solution space comprising for a given set of constraints and for all available resources of a specific kind—in this example: for doctors Dierickx and Peeters—is filtered to select all possible combinations for the selected resource—in the example of FIG. 1: for doctor Dierickx, in the example of FIG. 2: for doctor Peeters.

The user interface is arranged so that when a further resource is selected in addition to an already selected resource the additional information pertaining to the additional resource is additionally indicated in the displayed scheme.

In this particular embodiment, when doctor Peeters is selected in addition to doctor Dierickx, the additional available dates are at real time highlighted on the calendars.

Below aspects of the underlying scheduling method, more specifically of the method of generating a solution space, are described extensively.

Before explaining the general principles of the scheduling method, the method is first explained by working out a specific example, which is also one specific embodiment of the current invention.

According to the example, an appointment needs to be scheduled to examine a patient by means of a scanner. The patient needs to undress before and to dress again after the scan.

The exam itself takes 2 hours. Both for undressing and dressing one hour is provided. After the patient has undressed, he does not want to wait for the exam. When the exam is finished, he accepts that he may have to wait up to one hour before he can dress again.

Figure 4:
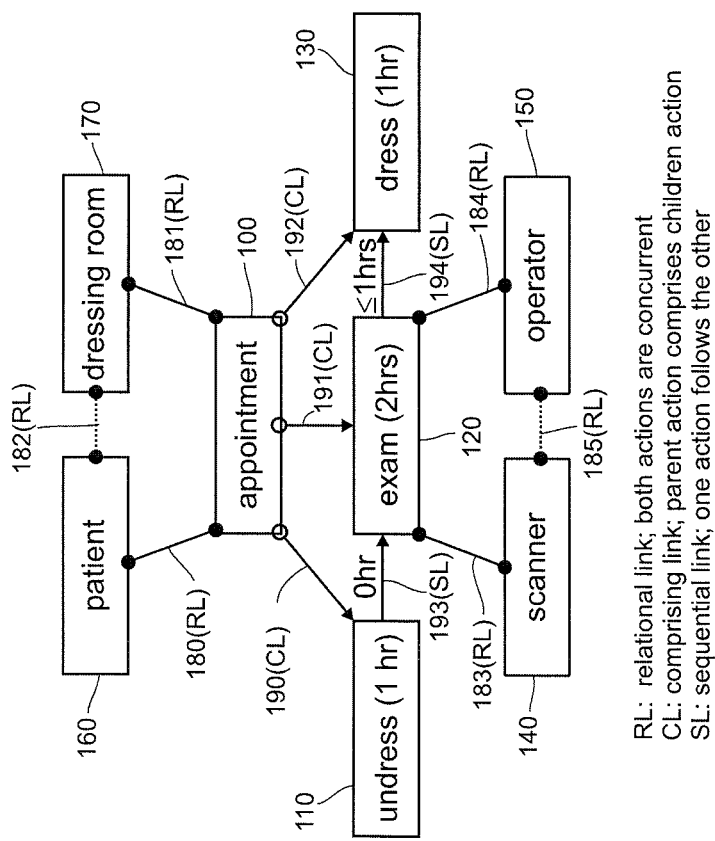
FIG. 4 describes a set of actions related to resources and connected by comprising, relational and sequential links.

FIG. 4 describes the actions that are part of the appointment and the relations between them. The appointment (100) action comprises three other actions: the undressing (110) action, the actual exam (120) action and the dressing (130) action. This comprising relationship is represented by three comprising links (190, 191, 192) between the individual actions (110, 120, 130) and the appointment (100) action. The appointment (100) action is called a parent relative to the undressing (110), the actual exam (120) and dressing (130) actions which are called children. Because of the parent-child relationship of a comprising link (190, 191, 192), it is not symmetrical.

An action is defined as being "atomic" when it does not comprise other actions. For example, the undress (110) action is atomic, but the appointment (100) action is not.

The undressing (110), the actual exam (120) and dressing (130) actions follow sequentially and this relationship is represented by the sequential links (193, 194). The sequential nature implies that such a link is not symmetrical, as the arrows in FIG. 4 also indicate.

The exam (120) can only be carried out when the scanner (140) is available. This kind of relationship is represented by a relational link (183). In addition does carrying out the exam require the availability of an operator, so a relational link (184) also exists between the exam and the operator (150). A relational link between two actions indicates that both actions can only be carried out at the same time. From this follows that such a link is by nature symmetrical and transitive. The transitivity is expressed in FIG. 1 by the dotted line (185) between the scanner and operator action.

In a more general case, a procedure or exam is preceded by a pre-op action and followed by a post-op action. In a more general case an action refers to an activity related to a resource. Such a resource can be a patient, a physician, a nurse, an operator a diagnostic or treatment apparatus, a examination or treatment room, or any other kind of resource with which an activity can be associated. The resource can or can not be related to the domain of healthcare. The activity can be the use of equipment, the presence of a person, the occupation of a facility or any other activity that refers to the use or availability of any resource. In a more general case any topology of any number of actions related by comprising, relational or sequential links is possible.

Figure 8:
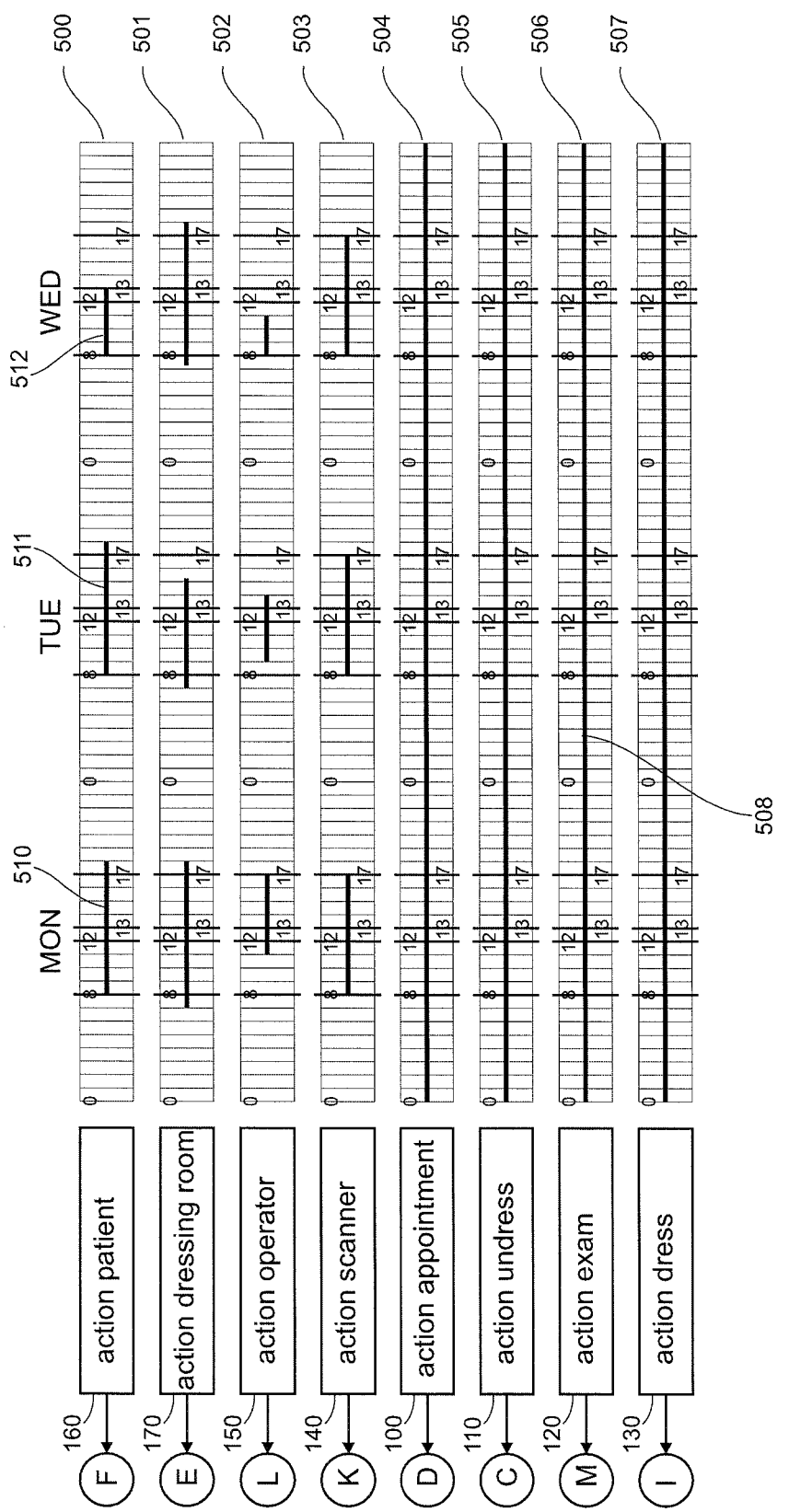
FIG. 8 describes a set of time windows associated with actions.

FIG. 8 shows how with each action (100, 110, 120, 130, 140, 150, 160, 170) in FIG. 4 a corresponding time window (501-507) is associated. A time window consists of a linked list of non contiguous time segments, each segment having a beginning and an ending time. For example, for the patient (160) action, the linked list consists of the time segments (510, 511, 512).

A time window can represent the range of time when an action can potentially occur. However, a time window can also represent a range of time when the action can start or when it can end.

In the example in FIG. 8, the time windows (500-503) of the patient (150), the dressing room (170), the scanner (140) and the operator (150) are part of the problem definition data. These time windows represent constraints imposed by the corresponding resources. The time windows (504-507) of the undressing (110), exam (120) and dressing (130) actions and of the appointment (100) as a whole, however, are initially undetermined, as they are the subject of the solution that has to be calculated for the scheduling problem. An undetermined time window is represented as one contiguous time segment with the length of the time window. For example, 508 is the initial time window associated with the exam action (120). As a solution for the time scheduling problem is being processed according to the current invention, the number of segments of an undetermined time window may change and the beginning and end times of the remaining time segments may become increasingly more focused, until they represent a situation that is consistent with all the constraints imposed by the resources.

Since the constraints imposed by the resources are represented by relational (180-185), comprising (190-192) and sequential (193, 194) links, processing the solution essentially comes down to working out these links.

When working out the links, a number of different cases are to be distinguished that correspond with the different nature of the links (relational, comprising or sequential), the interpretation of the time window of the action (start times, end times or action times), and the relative location of the time segments (the way that the time segments in the time windows of the linked actions overlap).

The result of processing a link involves adjusting the time segments in the time windows corresponding to the linked actions in a way that they become consistent with the constraints imposed by the corresponding resources.

In the following paragraphs the processing of the different links is discussed.

Figure 9:
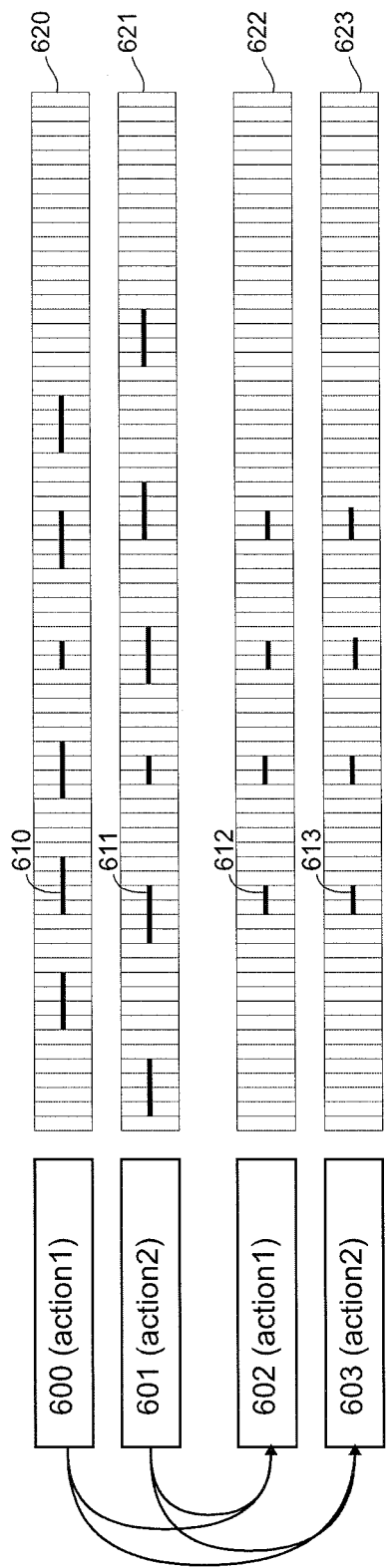
FIG. 9 demonstrates the processing of a relational link according to a preferred embodiment.

First Case: Time Window Processing for Actions Connected Through Relational Links FIG. 9 illustrates a number of situations for actions connected through relational links, of which the time segments occur in different relative positions (overlapping and non-overlapping). The interpretation of the time windows (620-623) is that the represent the time during which the action (600-603) can take place. Since the meaning of a relational link is that the two actions (600,601) can only take place simultaneously, the effect of working out the link is that each time window (620,621) should be replaced by a time window (622,623) that consists of time segments (612,613) that are the cross sections of the time segments (610,611) in the original time windows.

Because of the transitive nature of a relational link, if an action has more than one relational link—directly or indirectly—to another action, the time windows of all the actions are to be replaced by a time window of which the time segments are the cross sections of all the time segments of the time windows of all the related actions.

Figure 10:
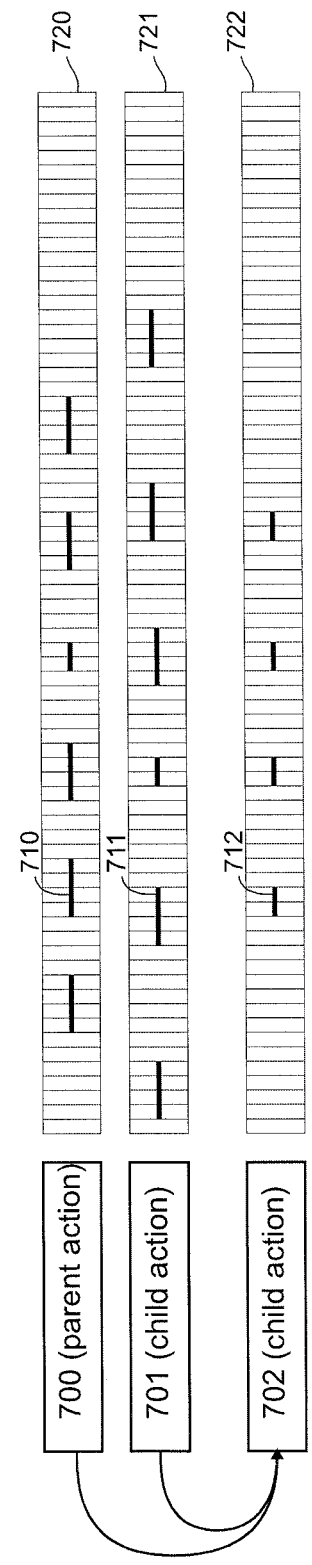
FIG. 10 demonstrates the processing of a comprising link according to a preferred embodiment.

Second Case: Time Window Processing for Actions Connected Through Comprising Links FIG. 10 illustrates a number of situations for actions connected through comprising links, of which the time segments occur in different relative positions (overlapping and non-overlapping). The interpretation of the time windows (700-702) is that the represent the time during which the action can take place. The meaning of a comprising link is that the time segments (711) of a child action (701) have to occur within the time segments (710) of the time window (720) of the parent action (700). This is achieved by replacing the time segments (711) of the time window (721) of the child action (701) by the cross section (712) of themselves (711) with the time segments (710) of the time window (720) of the parent action (700).

Third Case: Time Window Processing for Actions Connected Through Sequential Links The following terms are introduced or clarified:
time window of an action: linked list of time segments describing when an action can take place.
time window of start times of an action: linked list of time segments describing when said action can start;
time window of end times of an action: linked list of time segments describing when said action can end;
The time window of an action, the time window of start times of the same action and the time window of end times of that same action are interrelated.

Referring to FIG. 12 and according to an embodiment of the current invention, a time window (921) representing start times (911) of an action is calculated from a corresponding time window (920) representing said action, by subtracting from the end times of the time segments (910) in the latter time window (920) the duration (930) of said action.

Referring to FIG. 11 and according to an embodiment of the current invention, a time window (821) representing end times is of an action is calculated from a corresponding time window (820) representing said action, by adding to the start times of the time segments (810) in the latter time window (820) the duration (830) of the action.

According to an embodiment of the current invention time windows representing start times and end times of an action are also interrelated by shifting the start and end times in the time segments by the duration of the action.

According to one embodiment of the current invention, when a first preceding action (800, 902) is followed by a second following action (802, 900), certain restrictions are applied on both the start and end times of both actions.

A first restriction involves the start times of a following action in order to achieve that that the start times of a following action can never be earlier than the earliest end time of any of the preceding actions. According to one aspect of the current invention, this effect is achieved by replacing the time segments (813) of the start times (823) of the following action (802) by the cross section (814) between themselves (813) and the time segments (811) of the end times (821) of the preceding action (800).

A second restriction involves the end times of the preceding action in order to achieve that the end times of a preceding action can never be later than the latest start times of any of the following actions. According to one aspect of the current invention, this effect is achieved by replacing the time segments (913) of the end times (923) of the preceding action (902) by a cross section (914) between themselves (913) and the time segments (911) of the start times (921) of the following action (900).

Figure 13:
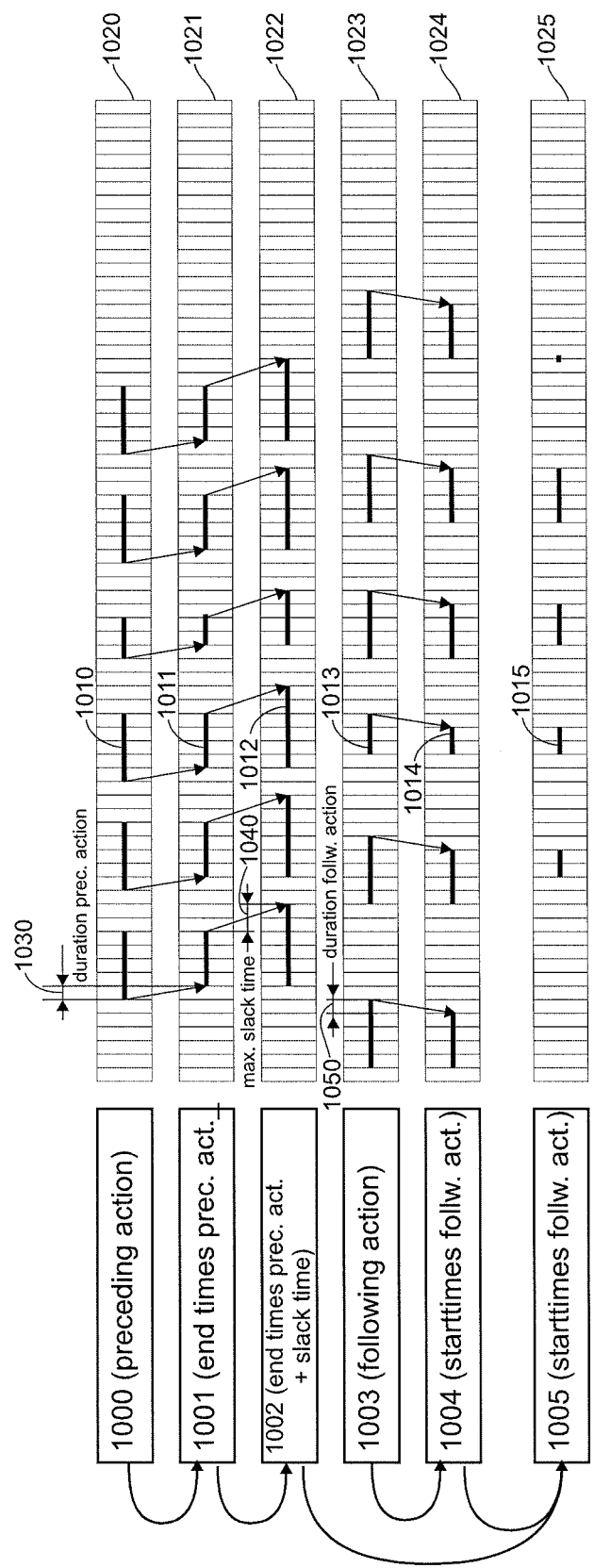
FIG. 13 demonstrates the processing of a sequential link with a following action, taking into account slack time according to a preferred embodiment.

In the case that slack time is allowed between two actions, the end times of the time segments of the preceding action are preferably extended by the maximum allowed slack time, prior to applying said first restriction. Referring to FIG. 13, the time window (1020) of the preceding action (1000) is used to calculate the time window (1021) of the end times (1001) of the preceding action (1000) by shifting the start times of the time segments (1010) forward by the duration (1030) of the preceding action (1000). Following that, the segments (1011) of the time window (1021) of the end times (1001) of the preceding action are extended by the maximum slack time (1040) to yield the time segments (1012) of the time window (1022) of the end times (1002) of the preceding action plus the slack time. To obtain the time window (1024) of the start times of the following action (1004), the end times of the segments (1013) of the time window (1023) of the following action (1003) are shifted backwards by the duration (1050) of the following action (1003). The segments (1015) of the time window (1025) of the start times of the following action (1005) are obtained by making the cross section between the time segments (1012) and the time segments (1014).

Working out a sequential link between two actions involves applying the two above restrictions.

Having described how according to the current invention:
relational links are processed (1);
composite links are processed (2);
the relation between time windows representing actions, start times and end times (3) is processed;
sequential links are processed (4);
slack time is processed in sequential links (5).
we proceed next by working out the example that was earlier introduced according to the principles of the current invention.

The problem that has to be resolved is finding the time window representing the start time(s) for the exam.

A first step consists of working out the relational links in FIG. 4.

Figure 14:
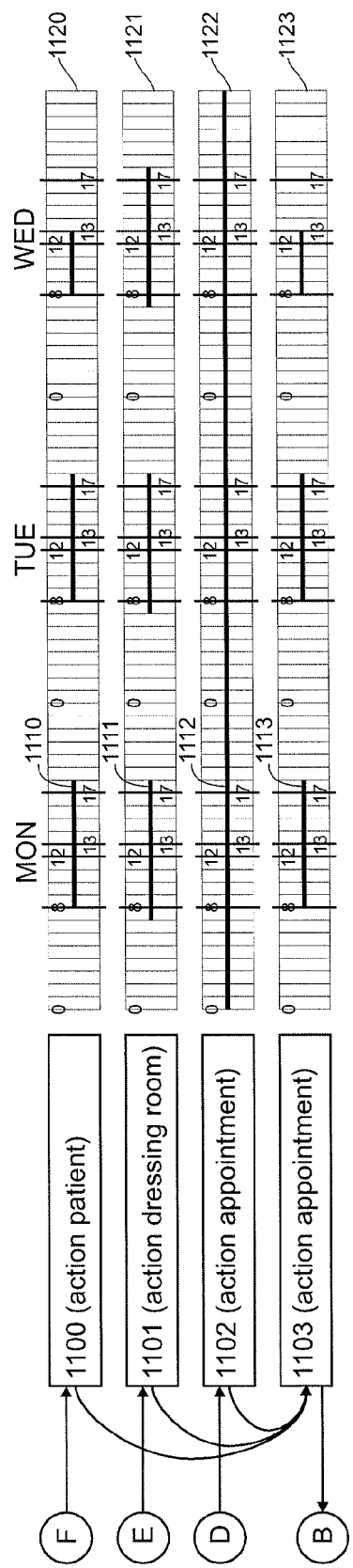
FIG. 14 shows an example of processing a relational link according to a preferred embodiment.

Referring to FIG. 14, this is done by using the general principles according to the current invention that were earlier explained by means of FIG. 9.

Figure 15:
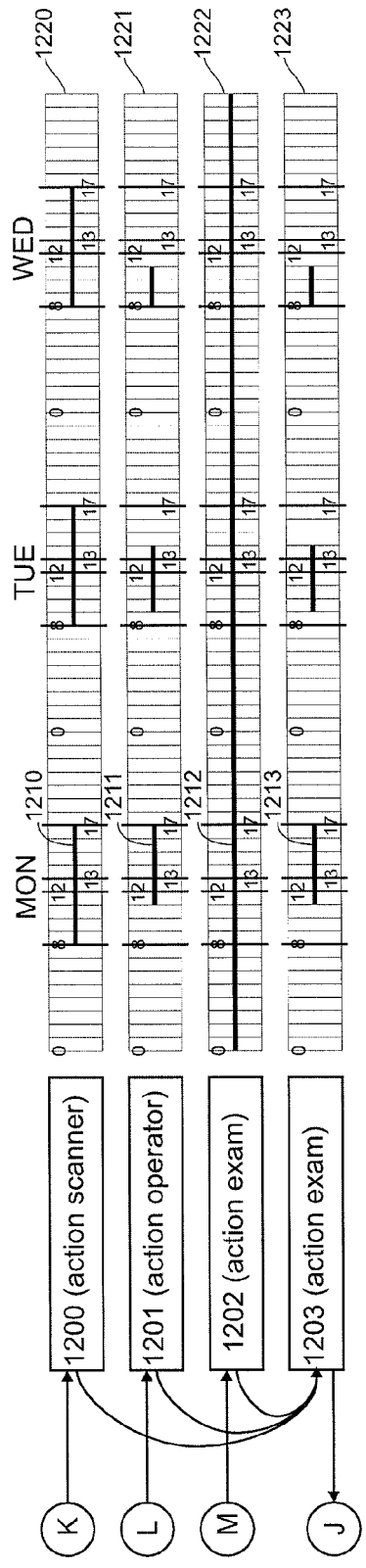
FIG. 15 shows another example of processing a relational link according to a preferred embodiment.

Similarly, referring to FIG. 15, the relational links can be worked out between the exam, the operator and the scanner.

Figure 5:
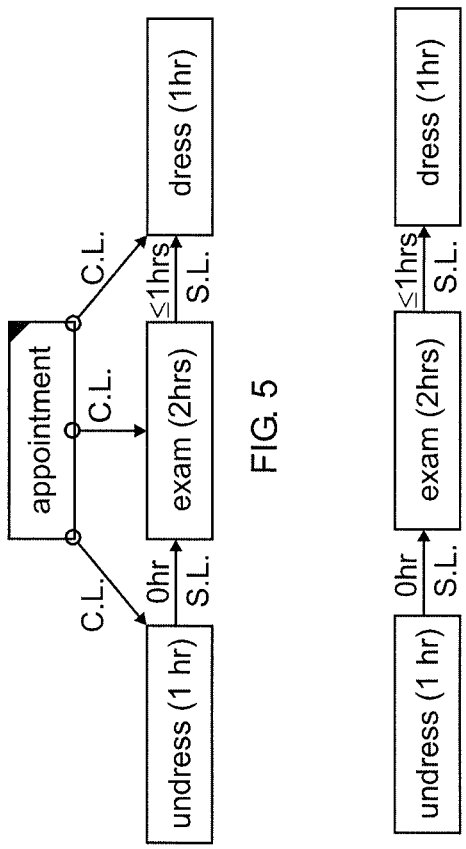
FIG. 5 describes a reduced set of actions that is left after working out the relational links according to a preferred embodiment.

After this operation, the graph in FIG. 4 can be reduced to the one in FIG. 5, with the notion that he time windows associated with the appointment and the exam actions are not the original ones, but the ones that were obtained from the previous step.

Figure 16A:
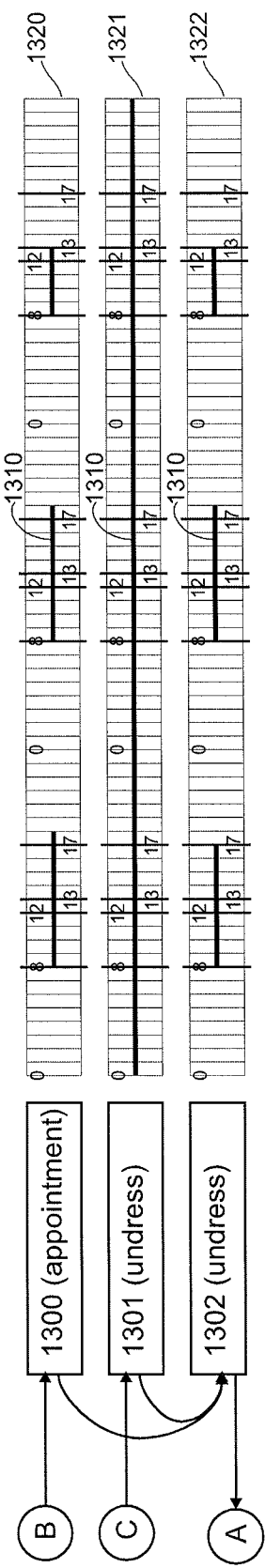
FIG. 16 shows three examples of processing a comprising link according to a preferred embodiment.
Figure 16B:
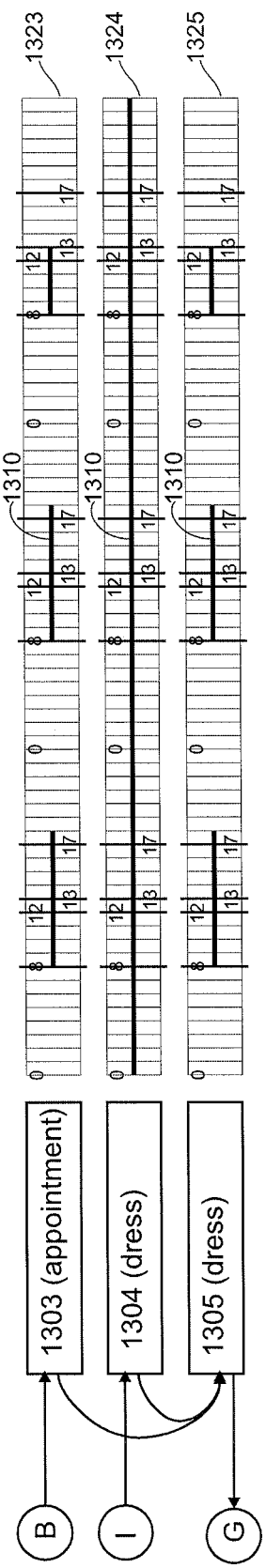
Figure 16C:
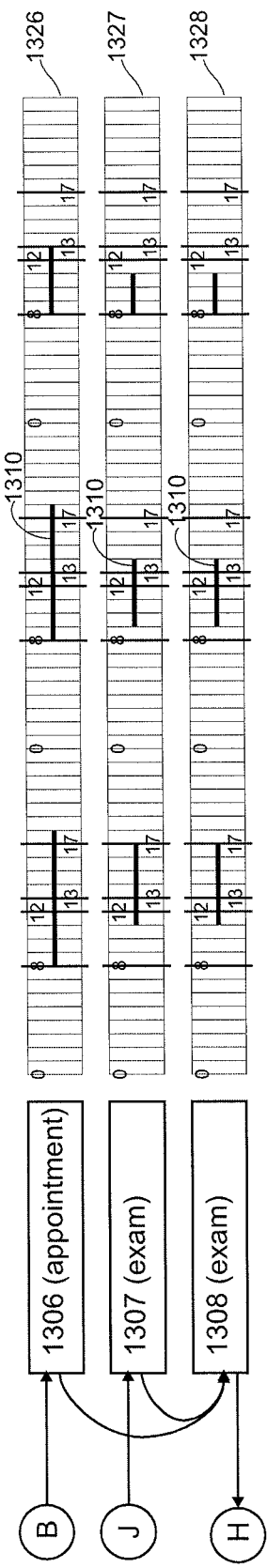

A second step consists of working out the comprising links in the graph in FIG. 5. According to the current invention, this is achieved by processing the time segments in the time windows of the undress, exam and dress actions so that they fall within the time segments of the time window of the appointment action. This is demonstrated in FIGS. 16A, 16B and 16C using the general principles of the current invention that were earlier explained by means of FIG. 10.

Figure 6:
FIG. 6 describes a reduced set of actions that is left after working out the relational and comprising links according to a preferred embodiment.

After this operation, the graph in FIG. 4 or FIG. 5 can be reduced to the one in FIG. 6, with the notion that he time windows associated with the undress, exam and dress actions are not the original ones, but the ones that were obtained from the previous step.

The third step consists of working out the constraints imposed by the sequential links.

The exam action is preceded and followed by another action. According to one aspect of the current invention, this has implications on start and end times of the time segments of the corresponding time windows.

Figure 17:
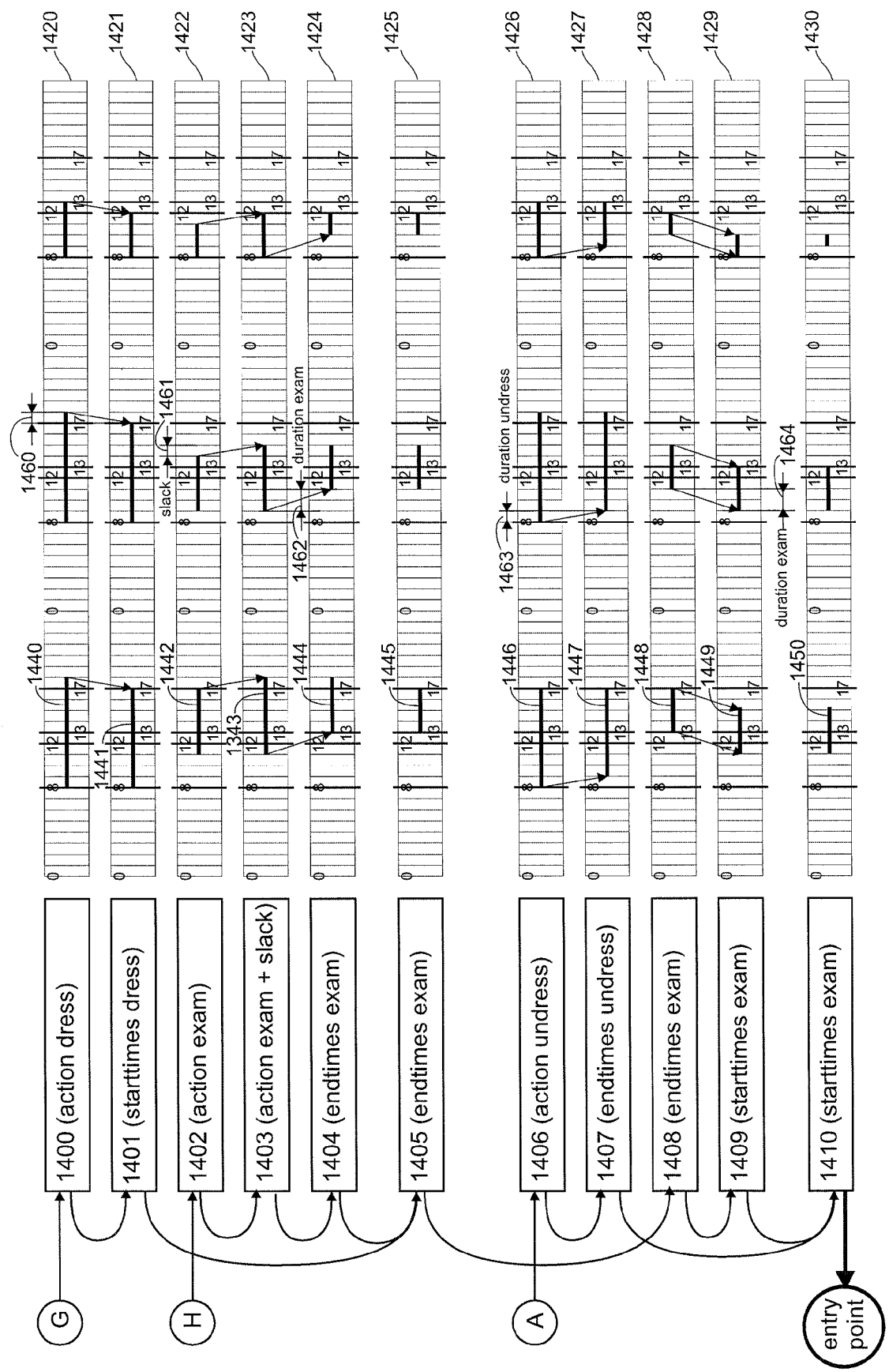
FIG. 17 shows an example of the processing of time windows according to a preferred embodiment.

Referring to FIG. 17, the start times (1310) of the exam should never be earlier than the earliest end times (1307) of the undress action, and the end times (1303) of the exam including slack time should never be later than the latest start times (1301) of the dressing action, according to the general principles that were earlier explained by means of FIGS. 11, 12 and 13.

Figure 7:
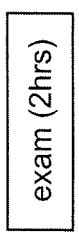
FIG. 7 describes a reduced set of actions that is left over after working out the relational, comprising and sequential links according to a preferred embodiment.

After this operation, the graph in FIGS. 4, 5 and 6 can be reduced to the one in FIG. 7, with the notion that he time window associated with the exam actions are the ones that were obtained from the previous step.

Introducing Deductive and Inductive Logic

According to a preferred embodiment of the current invention, an inductive logic method is used to control the processing of the time windows as opposed to deductive logic. These terms are explained in more detail.

Generally speaking, deductive logic starts with variables of which the values are known (called "the hypotheses") and deduces step by step according to a predefined flow the value of the variable for which a solution is sought (called the "final conclusion"). This processing occurs through the calculation of the value of intermediate values (called "intermediate conclusions").

In deductive logic, the information processing flow itself is the subject of the programming and as a result, once it has been programmed, it is fixed. Therefore, deductive logic programming is efficient for those problems of which the taxonomy of relations between variables is fixed, and only the values of the hypotheses are subject to change.

An example of a deductive logic method is shown in FIG. 18. H1, H2 and H3 are the basic hypotheses. Processing (151) the hypothesis H2 results in the intermediate conclusion C1. Processing (152) the conclusion C1 and the hypothesis H1 results in the intermediate conclusion C2. Processing (153) the conclusion C2 and the hypothesis H3 then leads to the final conclusion C3.

In contrary, the entry point for an inductive logic method according to the current invention is the final conclusion itself of which the value is initially unknown. By means of a set of inductive steps that take the form of an exploration process, the data of the hypotheses is first gathered and then systematically processed to calculate the final conclusion.

An inductive step to calculate an (intermediate) conclusion comprises determining what other variables are needed to calculate said (intermediate) conclusion. There are two possibilities:
1) Either the values of the variables that are needed are known because they are either hypotheses or intermediate conclusions of which the value has been earlier determined; in that case the variables can be processed to obtain the (intermediate) conclusion.
2) Or at least one of the variables that are needed is an intermediate conclusion of which the value has not been determined yet; in that case this (intermediate) conclusion initiates a new inductive step.

The subject of the programming in an inductive logic method is not a deductive information processing flow, but a rule set that manages the inductive steps.

Developing a rule set for an inductive method involves determining:
1) the nature (classes) of the variables (intermediate conclusions) that are needed to calculate a conclusion;
2) for each nature (class) of a variable (intermediate conclusion) determining what kind of processing on what other variables (other intermediate conclusions or hypotheses) is needed to calculate the result of said (intermediate) conclusion.

Unlike in a deductive logic method, the problem definition now not only states the values of the hypothesis, but also the taxonomy of the relations between the variables. This allows for far greater flexibility when solving problems that have different taxonomies of relations between variables. Once the rule set has been programmed, problems with a wide variety of taxonomies of relations between the above variables can be solved using the same program.

An example of using an inductive logic method is presented in FIG. 19. The entry point is a call to calculate the value of the variable C3. The rule set dictates that the variable C3 requires the processing of two other variables being H3, of which the value is known since it is a hypothesis, and the intermediate conclusion C2, of which the value at this point is unknown. The latter causes a new inductive step to calculate the unknown variable C2. The rule set dictates that the variable C2 requires the processing of two other variables H1, of which the value is known since it is a hypothesis, and of the intermediate conclusion C1, of which the value at this point is unknown. The latter causes a new inductive step to calculate C1. The rule set dictates that the variable C1 requires the processing of the variable H2, of which the value is known. This results in the processing of H2 to obtain C1. Now that C1 is known, this results in the processing of C1 and H1 to calculate C2. Now that C2 is known, this results in the processing of C2 and H3 to calculate the final conclusion C3.

PREFERRED EMBODIMENT BASED ON INDUCTIVE LOGIC

According to the current invention, the solution of the scheduling problem stated in the above example is preferably carried out by using an inductive logic method.

According to one embodiment, the following classes or variables are used for managing resources:
time window related to an action
time window related to the start times of an action
time window related to the end times of an action According to the same embodiment the inductive logic is managed by a set of three rules:
a first rule dictates that obtaining the value of a variable of the type "start times of an action" requires the processing of the value of the "end times of that action" and the value of "the previous action".
a second rule dictates that obtaining the value of a variable of the type "action" requires the processing of the values of the "parent actions" and the "related actions".
a third rule dictates that obtaining the value of a variable of the type "end times of an action" requires the processing of that same "action", the "slack time" and "the following action".

In a more general case other sets of rules can be selected that however yield equivalent results and also fall within the scope of the current invention. This follows from the fact that the classes of variables in the above rule set are related to each other by simple relationships.

We have found that the above set of three classes of variables in combination with the above three rules provides a self contained method than enables resource scheduling and management of a wide variety of situations.

The method according to the current invention processes time windows and results in a time window that generally comprises a plurality of time segments, each one indicating a single solution of when the corresponding action can take place (or start). The method hence produces not just one solution for the scheduling problem, as in the prior art, but a complete set of solutions also called a solution space.

The method according to the current invention can be used for any resource scheduling and management problem that can be modelled as a set of actions corresponding to resources that are related by a combination of comprising, relating and sequential links and slack time.

Having described the general principles of the current invention we proceed by working out the example that was earlier introduced.

Referring to FIG. 17, the method starts by instantiating a variable start times exam, which is the final conclusion of the scheduling problem.

The symbols in the circles on one of the FIGS. 14 to 17 indicate references to the same symbols in circles in one of the other figures.

Since the value of the variable start times exam at this point is unknown, this induces an inductive step (IS1). The first rule according to the current invention dictates that in order to calculate the value (1410) of the start times of the exam, the values (1408=1405) of the end time of the exam action and (1406=1302) of the undress action are needed. Since none of these values are known at this time, this causes two new inductive steps: a first one (IS2) to enable the calculation of the value (1406=1302) of the undress action and a second one (IS3) for the calculation of the value (1408=1405) of the end times of the exam.

We proceed by first explaining the inductive step (IS2). Referring to FIG. 14 to 17, the second rule dictates that in order to calculate the value (1406=1302) of the undress action requires the processing of the value (1300=1103) of the appointment action which is the parent action. Since the value (1300=1103) of the appointment action is not known at this time, this induces again an inductive step (IS4) for the calculation of that variable. Since this variable (1300=1103) appointment is of the type "action", the same (second) rule applies, requiring the processing of the values of related dressing room (1101) and patient (1100) actions. The values of these actions are known since they are hypotheses, so this enables to calculate the value of the appointment (1300=1103) action and subsequently of the undress (1406=1302) action.

We next proceed by describing the inductive step (IS3). Referring to FIG. 14 to 17, the third rule dictates that the calculation of the value (1408=1405) of the end times of the exam requires the processing of the value (1402=1308) of the exam action and of the value (1400=1305) of the dress action. Since the variable (1402=1308) of the exam action is of the type "action", the second rule applies, and this requires the processing of the values of the parent appointment (1306=1103) action, and of the related scanner (1200) and operator (1201) actions. The value (1306=1103) of the parent appointment action is calculated the same way as in the inductive step (IS2). The values (1200, 1201) of the relating actions are known, since they are hypotheses, so this enables to calculate the value of the exam (1402=1308) action. Since the variable (1400=1305) is also of the type action, the second rule is applied once more, leading to the processing of the values of the variables (1303=1103) and (1304=1101). At this point the calculation of the value (1408=1405) of the end times of the exam can be completed and subsequently the calculation of the value (1410) of the start times of the exam.

The above mentioned invention is preferably implemented using a data processing system such as a computer. An embodiment of such a system (1700) is shown in FIG. 20. A computer comprises a network connection means (1750), a central processing unit (1760) and memory means (1770) which are all connected through a computer bus (1790). The computer typically also has a computer human interface for inputting data (1710, 1720) and a computer human interface for outputting data (1730). According to one embodiment, the computer program code is stored on a computer readable medium such as a mass storage device (1740) or a portable data carrier (1800) which is read by means of a portable data carrier reading means (1780).

Having described in detail preferred embodiments of the current invention, it will now be apparent to those skilled in the art that numerous modifications can be made therein without departing from the scope of the invention as defined in the appending claims.

The invention claimed is:

1. In a computer-implemented appointment scheduling system, a method of managing appointment solutions for multiple resources comprising:
   computing a solution space comprising for a given set of constraints all possible appointment solutions for a particular type of appointment using all resources available to that type of appointment over available times,
   storing said solution space in a memory,
   displaying said possible appointment solutions on a user interface that includes user selectable elements, which correspond to said resources,
   upon selection of said user selectable elements, filtering said solution space to include possible appointment solutions for said resources that correspond to said selected user selectable elements,
   upon deselection of said user selectable elements, filtering said solution space to remove possible appointment solutions for said resources that correspond to said deselected user selectable elements,
   displaying a result of said filtering in said user interface that is displayed on a display device,
   wherein said solution space is computed by:
      defining relationships between actions of available resources having associated action constraints, said actions being described by means of time windows comprising linked lists of time segments describing ranges of start times or end times or duration times, said relationships belonging to the set comprising relational or sequential relationships;
      identifying a set of resources of a certain kind, and
      processing said time windows to determine possible solutions for the actions of the identified resources; wherein said processing comprises an inductive logic step,
   the inductive logic step comprises obtaining a time window of end times of an action by processing a time window of said action, a time window of a following action and a slack time, and
   the inductive logic step of obtaining a time window of end times of an action by processing a time window of said action, a time window of a following action and a slack time further comprises:
      subtracting the duration from the end times of the time segments of the time window of said following action to obtain a time window of start times of said following action;
      adding the slack time to the end times of the time segments of the time window of said action to obtain a time window of said action plus slack;
      adding the duration to the start times of the time segments of the time window of said action plus slack to obtain a time window of end times of said action; and
      obtaining a time window of end times of said action of which the time segments are the cross section of the time segments of a time window of start times of said following action and the time segments of a time window of end times of said action.

2. The method according to claim 1, wherein the inductive logic step comprises obtaining a time window of start times of an action by processing a time window of end times of said action and a time window of a previous action.

3. The method according to claim 2, wherein the inductive logic step of obtaining a time window of start times of an action by processing a time window of end times of said action and a time window of a previous action further comprises:

adding the duration of said previous action to the start times of the time segments of the time window of said previous action to obtain a time window of the end times of said previous action;

shifting the time segments of the time window of the end times of said action backward by the duration of said action to obtain a time window of the start times of said action; and obtaining a time window of the start times of said action of which the segments are the cross section of the segments of the time window of the end times of the previous action and the segments of the time window of the start times of said action.

4. The method according to claim 1, wherein the inductive logic step comprises obtaining a time window of an action by processing the time windows of actions that are either a parent action or related actions.

5. The method of claim 4, wherein the inductive logic step of obtaining a time window of an action by processing the time windows of actions that are either a parent action or related actions comprises:

replacing the time segments of time windows of related actions by time segments that are the cross sections of the original time segments of said time windows of said related actions;

adjusting the begin and end times of time segments of children actions to be included in the time segments of the time window of the parent action.

6. The method according to claim 1, wherein at least one of said resources is a patient, a physician, a nurse, a medical diagnostic apparatus, a medical treatment apparatus, an examination room or a treatment room.

7. The method according to claim 1 wherein upon selection of an additional resource said filtering of the solution space is repeated for the additional resource and wherein the result of said filtering is additionally displayed.

8. The method according to claim 1 wherein said result is displayed in the form of highlighted data on a displayed calendar.

9. The method according to claim 1, wherein the filtering of said solution space to select all possible appointment solutions for said resources that correspond to said user selectable elements is performed in real time.

10. The method according to claim 1, wherein said result of said filtering is displayed on said user interface as a calendar, which includes dates and times of possible appointment solutions for said resources that correspond to said selected user selectable elements.

11. The method according to claim 1, wherein the user selectable elements are checkboxes that include names of the resources associated with the user selectable elements.

\* \* \* \* \*